(12) United States Patent
Giambattista et al.

(10) Patent No.: US 9,913,946 B2
(45) Date of Patent: Mar. 13, 2018

(54) MEDICAMENT DELIVERY DEVICE

(71) Applicant: SHL GROUP AB, Nacka Strand (SE)

(72) Inventors: Lucio Giambattista, East Hannover, NJ (US); Antonio Bendek, Vernon, NJ (US)

(73) Assignee: SHL GROUP AB, Nacka Strand (SE)

( * ) Notice: Subject to any disclaimer, the term of this patent is extended or adjusted under 35 U.S.C. 154(b) by 131 days.

(21) Appl. No.: 14/948,637

(22) Filed: Nov. 23, 2015

(65) Prior Publication Data

US 2016/0082197 A1 Mar. 24, 2016

Related U.S. Application Data

(63) Continuation-in-part of application No. 14/449,671, filed on Aug. 1, 2014, which is a continuation of (Continued)

(30) Foreign Application Priority Data

Dec. 15, 2009 (SE) ...................................... 0950958

(51) Int. Cl.
*A61M 5/00* (2006.01)
*A61M 5/178* (2006.01)
(Continued)

(52) U.S. Cl.
CPC ...... *A61M 5/31551* (2013.01); *A61M 5/3146* (2013.01); *A61M 5/3158* (2013.01);
(Continued)

(58) Field of Classification Search
CPC .......... A61M 5/31553; A61M 5/31561; A61M 5/3158; A61M 5/31536; A61M 5/31558;
(Continued)

(56) References Cited

U.S. PATENT DOCUMENTS 6,042,571 A 3/2000 Hjertman et al.
6,221,053 B1 4/2001 Walters et al.
(Continued)

FOREIGN PATENT DOCUMENTS

DE 102004063652 7/2006
WO 01/95959 12/2001
(Continued)

OTHER PUBLICATIONS

International Search Report and Written Opinion for International Patent App. No. PCT/US2010/060022.

*Primary Examiner* — Rebecca E Eisenberg
(74) *Attorney, Agent, or Firm* — McDonnell Boehnen Hulbert & Berghoff LLP

(57) ABSTRACT

A dose setting mechanism for a medicament delivery device is presented having a pinion mounted to a locking member where the axis of rotation of the pinion is offset and parallel to the longitudinal axis of the housing containing the dose setting components. Primary and secondary dose members are engaged with the pinion to indicate a set dose of medicament. A resetting mechanism is also presented where nut segments are threadedly engaged with an outer surface of a lead screw when in the locked position and are disengaged from the lead screw when the nut segments are in the unlocked position.

16 Claims, 10 Drawing Sheets

Related U.S. Application Data application No. 13/896,639, filed on May 17, 2013, now Pat. No. 8,827,962, which is a continuation of application No. 13/203,040, filed as application No. PCT/US2012/060022 on Dec. 13, 2010, now Pat. No. 8,491,536.

(51) Int. Cl.
*A61M 5/315* (2006.01)
*A61M 5/24* (2006.01)
*A61M 5/31* (2006.01)

(52) U.S. Cl.
CPC .... *A61M 5/31543* (2013.01); *A61M 5/31553* (2013.01); *A61M 5/31558* (2013.01); *A61M 5/24* (2013.01); *A61M 5/31561* (2013.01); *A61M 2005/2407* (2013.01); *A61M 2005/2477* (2013.01); *A61M 2005/2485* (2013.01); *A61M 2005/2488* (2013.01); *A61M 2005/3126* (2013.01); *A61M 2005/3154* (2013.01)

(58) Field of Classification Search
CPC .. A61M 2005/3126; A61M 2005/2047; A61M 5/24; A61M 5/31551
See application file for complete search history.

(56) References Cited

U.S. PATENT DOCUMENTS

| | | |
|---|---|---|
| 2003/0160072 A1* | 8/2003 | Geiser ............... A61M 5/24 222/327 |
| 2005/0165363 A1 | 7/2005 | Judson et al. |
| 2009/0275914 A1 | 11/2009 | Harms et al. |
| 2009/0275916 A1 | 11/2009 | Harms et al. |
| 2011/0306947 A1 | 12/2011 | Boyd et al. |
| 2012/0283648 A1 | 11/2012 | Veasey et al. |
| 2012/0302964 A1 | 11/2012 | MacDonald et al. |

FOREIGN PATENT DOCUMENTS

| | | |
|---|---|---|
| WO | 03/080160 | 10/2003 |
| WO | 2008/101829 | 8/2008 |

* cited by examiner

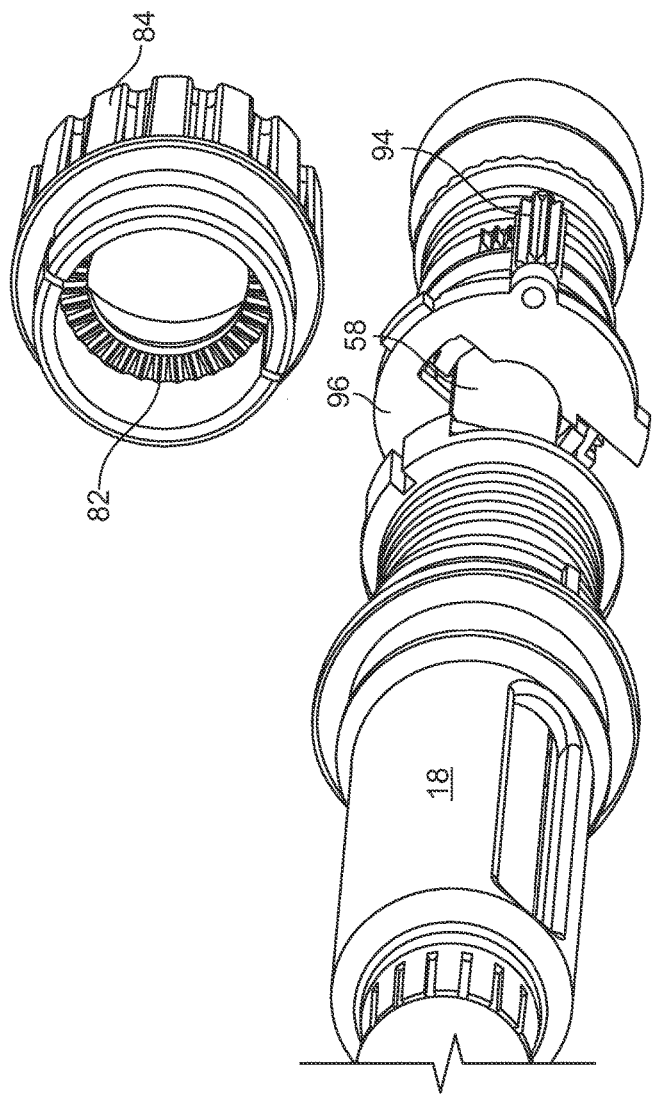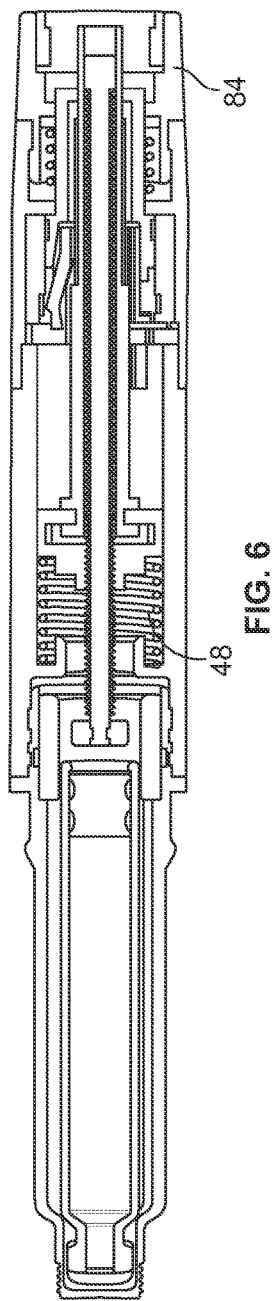
FIG. 5
FIG. 6

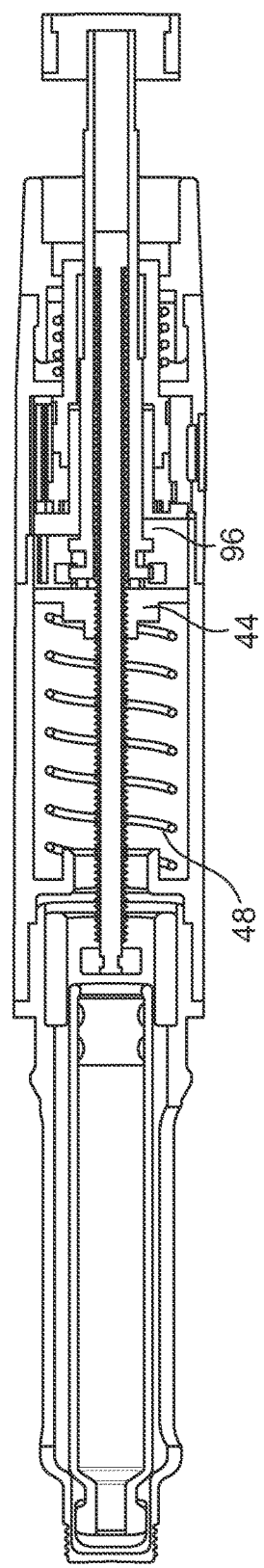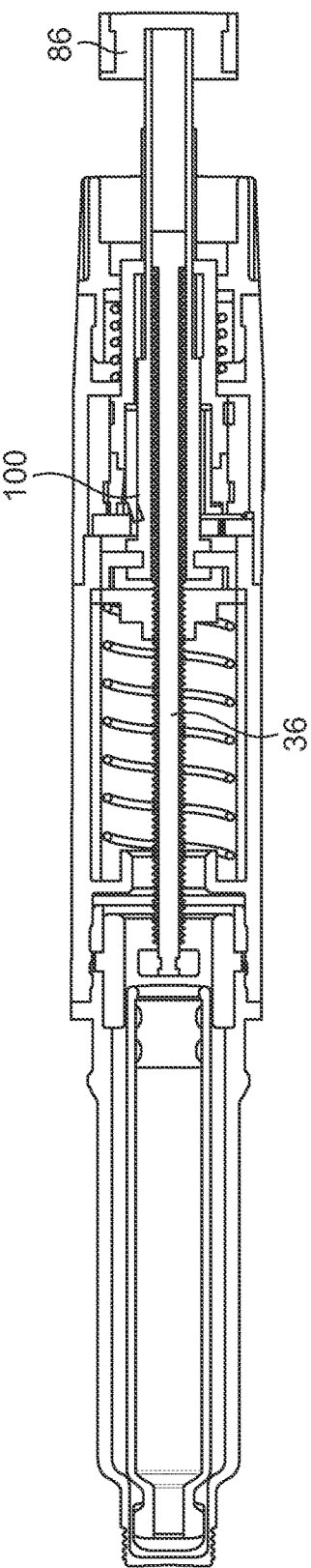
FIG. 7A
FIG. 7B

MEDICAMENT DELIVERY DEVICE

CROSS REFERENCE TO RELATED APPLICATIONS

The present application is a continuation-in-part of U.S. patent application Ser. No. 14/449,671, filed Aug. 1, 2014, which is a continuation of U.S. patent application Ser. No. 13/896,639, filed May 17, 2013, now U.S. Pat. No. 8,827,962, which is a continuation of U.S. patent application Ser. No. 13/203,040, filed Jan. 31, 2012, now U.S. Pat. No. 8,491,536, which is a U.S. National Phase Application pursuant to 35 U.S.C. § 371 of International Application No. PCT/US2010/060022 filed Dec. 13, 2010, which claims priority to Swedish Patent Application No. 0950958-9 filed on Dec. 15, 2009. The entire disclosure contents of these applications are herewith incorporated by reference into the present application.

TECHNICAL AREA

The present invention relates to a medicament delivery device comprising a dose setting function.

BACKGROUND

Medicament delivery devices such as injectors are sometimes provided with functions where a specific dose can be set by the user, which dose may be varied within a range.

Quite often this dose setting function is performed by turning a knob or wheel at the distal end of the device whereby it is moved in the distal direction. When performing a subsequent injection, the knob is pushed linearly in the proximal direction. One such injector is disclosed in the document U.S. Pat. No. 6,221,053 in which the distal dose knob of the injector is threaded out of a rod barrel tube as a dose is set. Thus the distance the knob is moved in the distal direction is directly related to the dose quantity to be delivered.

One drawback with that type of solution is that if larger doses are to be delivered the dose knob has to be moved quite a long distance in the distal direction, which means that it might be difficult for a user to push the dose knob in the proximal direction during injection. Another drawback of a number of available pen-type drug delivery devices is that they are not reusable in the sense that once the cartridge or vial of medicament is used or exhausted there is no way to remove the old cartridge to replace it with a new cartridge. In other words, once the cartridge is emptied the pen-type device must be thrown away and a new device obtained in order to continue with further administration of the medicament.

SUMMARY

The aim of the present invention is to remedy the drawbacks of the state of the art medicament delivery devices and to provide a device by which it is possible to set a desired or required dose in a simple and intuitive way, and to provide a mechanism whereby a new cartridge of medicament can replace an empty cartridge thus allowing the delivery device to be continuously used to delivery doses of medicament.

This aim is obtained by a medicament delivery device according to the features of the independent patent claim. Preferable embodiments of the invention are subject of the dependent patent claims.

According to a main aspect of the invention it is characterised by a medicament delivery device comprising a housing having opposite distal and proximal ends; a medicament container holder releasably connected to said housing; a medicament container arranged inside said medicament container holder; a threaded plunger rod arranged to pass through a first inner wall of the housing and arranged to act on a stopper in the medicament container; a lead screw member coaxially connected to the threaded plunger rod by co-acting first slidably-and-rotatably-locked means; wherein said device further comprises a nut coaxially connected to the threaded plunger rod by a treaded engagement between them, connected to the lead screw member by co-acting non-slidable-and-rotatable means, and connected to the housing by co-acting second slidably-and-rotatably-locked means; a primary dose member coaxially rotatable on the lead screw member when the device is in a non-activated state and connected to the lead screw member by co-acting third slidably-and-rotatably-locked means when the device is in an activated state; a locking member fixedly connected to the housing and releasably connected to the lead screw member by co-acting locking means; a first spring force means arranged between the first inner wall of the housing and the nut, wherein the first spring force means is in a pre-tensioned state when said locking means are engaged and the device is in the non-activated state; a secondary dose member rotatably connected to said primary dose member via a pinion gear; dose setting means connected to the primary dose member by co-acting fourth slidably-and-rotatably-locked means, such that when the device is to be set from the non-activated state to the activated state, the dose setting means are manually manipulated in a pre-determined direction, whereby the locking means are released and the lead screw member is distally moved a pre-determined distance by the first spring force means independent of the size of a dose to be set.

According to a further aspect of the invention, said primary and said secondary dose members are provided with indicia.

According to another aspect of the invention, the locking means comprises a proximally pointing and radial flexible lever arranged on the locking member, an annular ledge on the circumferential surface of the lead crew member, and the circumferential inner surface of the secondary dose member; such that when the first spring force means is in a pre-tensioned state, the circumferential inner surface of the secondary dose member forces the flexible lever radial inwardly in contact with the ledge; and when the dose setting means are manually manipulated, the secondary dose member is rotated to a position wherein the flexible lever is radial outwardly flexed into a longitudinal groove on the inner circumferential surface of the secondary dose member.

According to yet a further aspect of the invention, the locking member comprises on its distal circumferential surface a distally pointing stop member, and wherein the secondary dose member comprises on its proximal circumferential surface a first and a second proximally pointing stop members arranged to interact with the stop member of the locking member.

According to yet another aspect of the invention, the non-slidable-and-rotatable means comprises ratchet arms and radial inwardly directed arms on the nut, grooves on the outer circumference of wheels on the proximal end of the lead screw member, and an annular groove between the wheels, wherein the ratchet arms cooperate with the grooves for giving an audible signal when the lead screw member is rotated; and wherein the radial inwardly directed arms cooperate with the annular groove such that the lead screw member and the nut are slidably locked and rotatable in relation to each other.

According to a further aspect of the invention, the first slidably-and-rotatably-locked means comprises radial inwardly directed ledges on the inner surface of the proximal end of the lead screw member, and longitudinally extending grooves on the plunger rod, wherein the grooves cooperate with the radial inwardly directed ledges such that the lead screw member and the plunger rod are rotationally locked and slidable in relation to each other.

According to another aspect of the invention, the second slidably-and-rotatably-locked means comprises grooves on the outer circumferential side surface of the nut, and longitudinal ribs on the inner surface of the housing, wherein the grooves cooperate with the longitudinal ribs such that the nut and the housing are rotationally locked and slidable in relation to each other.

According to yet a further aspect of the invention, the third slidably-and-rotatably-locked means comprises splines on the outer circumferential surface of the lead screw member, and corresponding splines arranged on the inner circumferential surface of the primary dose member, wherein the splines cooperate with corresponding splines such that the lead screw member and the primary dose member are rotationally locked and slidable in relation to each other.

According to yet another aspect of the invention, the dose setting means comprises a clutch plate provided with a first annular ratchet, a dose setting knob provided with a second annular ratchet, and a second spring force means arranged between a second inner wall of the housing and a proximal surface of the clutch plate, such that clutch plate is distally urged and the first and the second ratchet are abutting each other, and which dose setting knob protrudes through the distal end of the housing.

According to a further aspect of the invention, the fourth slidably-and-rotatably-locked means comprises longitudinally extending grooves on the outer circumferential surface of the primary dose member, and radial inwardly directed protrusions on the inner surface of the clutch plate, wherein the longitudinally extending grooves cooperate with radial inwardly directed protrusions such that the primary dose member and the clutch plate are rotationally locked and slidable in relation to each other.

According to another aspect of the invention, the plunger rod is arranged to be proximally moved a distance corresponding to a set dose to be delivered by manually manipulating the dose setting knob when the device is in the activated state.

There are a number of advantages with the present invention. Because the lead screw, e.g. the manually operating delivery means, protrudes outside the housing with the same length independent of the set dose quantity the manual dose delivery operation is the same independent of set dose, i.e. the lead screw member has always the same position when a dose has been set.

Compared to the state of the art medicament delivery devices, this solution is a great advantage for the user or patient who suffers of dexterity problems. Also when not in use, the lead screw member is inside the medicament delivery device and locked. The unlocking of the lead screw member is performed when said dose setting knob is turned to an initial position, preferably a zero-dose position.

Another advantage of the present disclosure is the inclusion of a resetting mechanism that allows for an empty or exhausted cartridge of medicament to be removed from the device and replaced with a new full cartridge of medicament. This resetting mechanism can transform a disposable drug delivery device into a reusable drug delivery device. Resetting of the dose setting mechanism is accomplished by retracting the proximally extended lead screw distally back into the device a distance that allows a fresh cartridge of medicament to be inserted into the cartridge holder and then reconnected to drug delivery device. In one embodiment the lead screw resetting mechanism includes a housing having an outer surface on a proximal end configured to allow removable attachment of a cartridge holder through engagement of a snap fit connector on the outer surface. A locking shell is positioned inside the housing that has a radial projecting pin protruding through the outer surface of the housing, where the locking shell is rotatable relative to the housing and configured to engage the cartridge holder during attachment to the housing. A lock pin is rotationally fixed to the housing and can have a stop projecting through the outer surface of the housing and slidable in the distal direction from an unlocked to a locked position where the stop prevents removal of the cartridge holder from the housing. There is a biasing member that exerts a distal force on the lock pin to move the stop from the unlocked to the locked position and a transfer ring rotationally fixed to and axially slidable to the locking shell. A cam nut engages with the transfer ring through a cam that allows the transfer ring to rotate and move axially relative to the cam nut. A push pin axially fixed to the transfer ring and a nut segment slidably connects to the push pin through a cam, where the nut segment is configured to move from a locked position to an unlocked position.

A push plate can be present in the resetting mechanism to transfer a proximal biasing force to a cartridge contained in the cartridge holder, where the biasing member is preferably a compression spring located between the push plate and the lock pin. The resetting mechanism can have two nut segments that are threadedly engaged with an outer surface of a lead screw having a longitudinal axis when in the locked position and are disengaged from the lead screw when the nut segments are in the unlocked position. The nut segments are preferably engaged with the push pin such that nut segments simultaneously move transversely relative to the longitudinal axis of the lead screw when the push pin moves axially causing the nut segments to move from the locked to the unlocked position.

A method of resetting a drug delivery device is also disclosed where a first step includes placing a dose setting mechanism in a non-activated state. Preferably this is achieved when the dose button has been pushed in and locked after delivering a set dose of medicament and before the dose dial is reset to a zero dose, which would then cause the dose bottom to pop out the distal end of the housing indicating that the drug delivery device was now in an activated state. When in the non-activated state, the cartridge holder is rotated relative to a front housing of a resetting mechanism causing rotation of a locking shell within the front housing. This also causes simultaneous rotation of a transfer ring with the rotation of the locking shell to cause the transfer ring to move axially in the proximal direction relative to the locking shell following a cam track connecting the transfer ring to a cam nut that is rotationally fixed to the front housing. This then moves a push pin axially in the proximal direction as a result of the axially fixed connection to the transfer ring. Simultaneously, one or more nut segments are moved transversely from a locked position to an unlocked position as a result of a cammed engagement with the push pin. At this point the cartridge holder can be pulled off axially in the proximal direction to remove it from the front housing and the lead screw can be pushed axially in a distal direction to reset the drug delivery device such that a new cartridge of medicament can be loaded into the cartridge holder and the cartridge holder reattached to the front housing.

The resetting mechanism causes the nut segments, which start as threadedly engaged with an outer surface of the lead screw when in the locked position, to be disengaged from the lead screw when the nut segments are in the unlocked position.

These and other features and advantages will become apparent from the detailed description and from the accompanying drawings.

BRIEF DESCRIPTION OF THE FIGURES

In the detailed description reference will be made to the accompanying drawings in which FIGS. 1a,b are a cross-sectional view of a medicament delivery device according to the present invention;

FIG. 5 is yet a further detailed view of the dose-setting mechanism comprised in the present invention; and FIGS. 6, 7a, 7b, 8a, and 8b are cross-sectional view of different functional positions.

DETAILED DESCRIPTION

Figure 1:
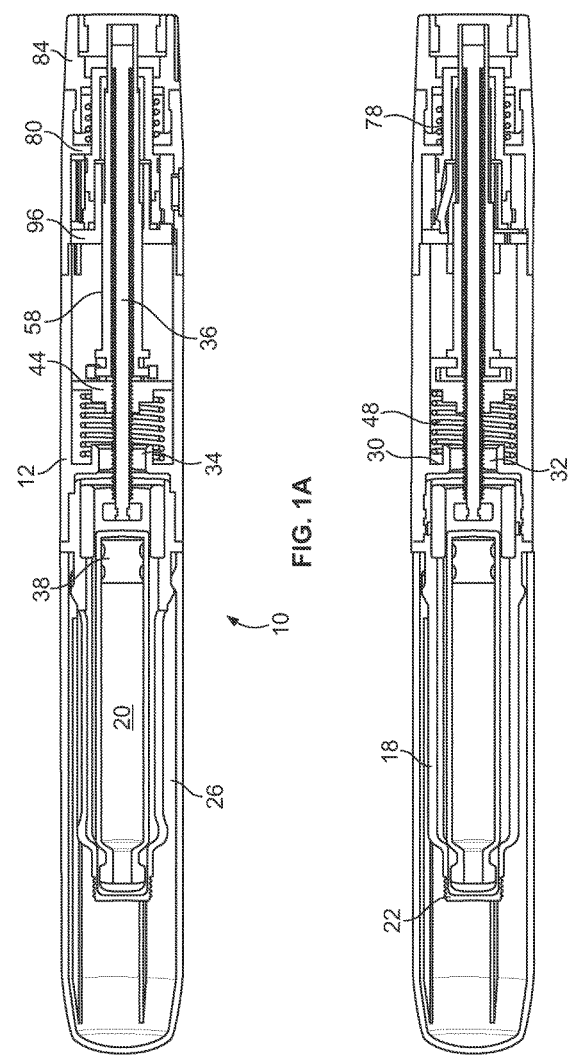

In the present application, when the term "distal part/end" is used, this refers to the part/end of the injection device, or the parts/ends of the members thereof, which under use of the injection device is located the furthest away from the medicament injection site of the patient. Correspondingly, when the term "proximal part/end" is used, this refers to the part/end of the injection device, or the parts/ends of the members thereof, which under use of the injection device is located closest to the medicament injection site of the patient.

The medicament delivery device 10 according to the drawings comprises a generally elongated housing 12 having opposite distal and proximal ends. The elongated housing being e.g. divided in a proximal 12a and a distal part 12b. The proximal end of the housing is arranged with fastening means such as e.g. threads 14 on its inner surface, which fastening means cooperate with corresponding fastening means such as outwardly threads 16 on a distal end of a medicament container holder 18, providing a releasable connection. Inside the medicament container holder a medicament container 20 can be placed. The proximal end of the medicament container holder 18 is arranged with a threaded neck 22 for connection of a medicament delivery member such as an injection needle 24, a mouthpiece, a nozzle or the like, FIG. 2.

When received by a user, the medicament delivery device 10 is provided with a releasably attachable protective cap 26. At the distal end of the medicament container holder a sleeve-shaped container support 28 is inserted for holding and supporting the medicament container 20 when inserted, FIG. 2. At the proximal end of the housing a first inner wall 30 is arranged, which wall is provided with a central passage 32, FIG. 1b. The central passage is arranged with a distally directed tubular flange 34, FIG. 1a. A threaded plunger rod 36 extends in the longitudinal direction through the central passage 32 with a proximal end adjacent a stopper 38 inside said medicament container 20, FIG. 1a. The proximal end of the plunger rod 36 is further arranged with a plunger rod tip 40, FIG. 2.

The device further comprises a lead screw member 58 coaxially connected to the threaded plunger rod by co-acting first slidably-and-rotatably-locked means; and a nut 44 coaxially connected to the threaded plunger rod by a treaded engagement between them. The nut also being connected to the lead screw member by co-acting non-slidable-and-rotatable means, and to the housing by co-acting second slidably-and-rotatably-locked means.

Figure 2:
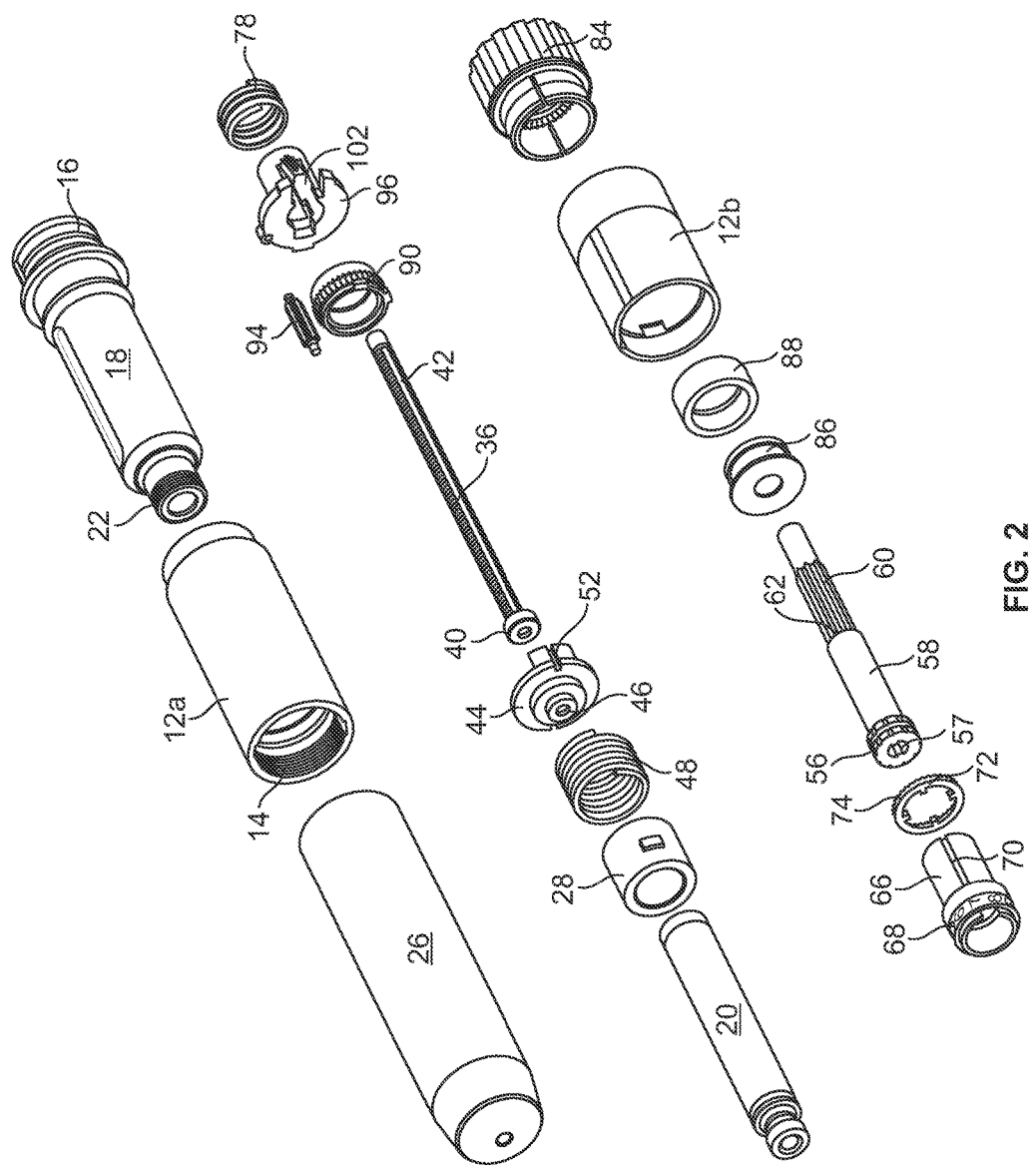
FIG. 2 is an exploded view of the medicament delivery device of FIGS. 1a,b.

The first slidably-and-rotatably-locked means comprises radial inwardly directed ledges 57 on the inner surface of the proximal end of the lead screw member, and longitudinally extending grooves 42 on the plunger rod, FIG. 2, wherein the grooves cooperate with the radial inwardly directed ledges 57 such that the lead screw member and the plunger rod are rotationally locked and slidable in relation to each other.

Figure 3:
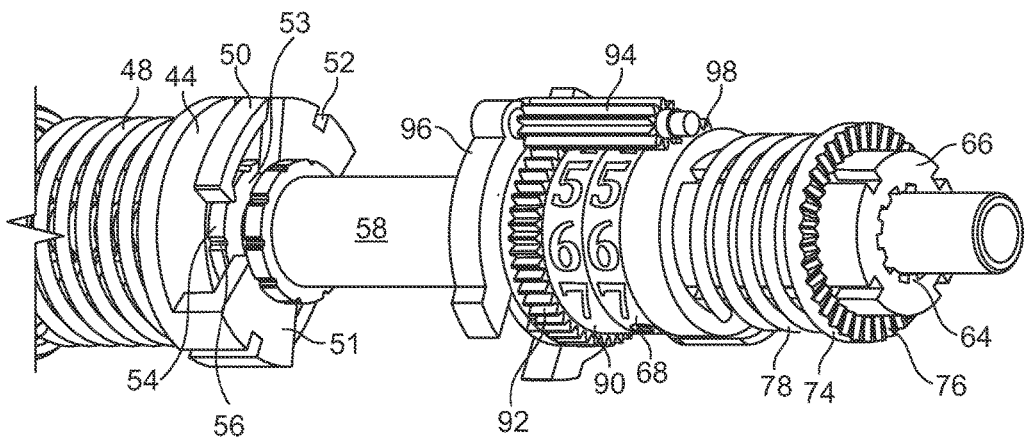
FIG. 3 is a detailed view of a dose-setting mechanism comprised in the present invention.

The non-slidable-and-rotatable means comprises ratchet arms 50 and radial inwardly directed arms 51 on the nut 44, grooves 56 on the outer circumference of wheels 54 on the proximal end of the lead screw member, and an annular groove 53 between the wheels 54, wherein the ratchet arms 50 cooperate with the grooves 56 for giving an audible signal when the lead screw member is rotated; and wherein the radial inwardly directed arms 51 cooperate with the annular groove 53 such that the lead screw member and the nut are slidably locked and rotatable in relation to each other, FIG. 3.

The second slidably-and-rotatably-locked means comprises grooves 52 on the outer circumferential side surface of the nut 44, FIG. 3, and longitudinal ribs on the inner surface of the housing (not shown), wherein the grooves cooperate with the longitudinal ribs such that the nut and the housing are rotationally locked and slidable in relation to each other.

The nut 44 comprises a threaded central passage 46 which cooperates with the threads of the plunger rod, FIG. 2, thereby forming the threaded engagement between them.

The device also comprises a primary dose member 66 coaxially rotatable on the lead screw member when the device is in a non-activated state and connected to the lead screw member by co-acting third slidably-and-rotatably-locked means when the device is in an activated state. The third slidably-and-rotatably-locked means comprises splines 60 on the outer circumferential surface of the lead screw member; and corresponding splines 64 arranged on the inner circumferential surface of the primary dose member, wherein the splines 60 cooperate with corresponding splines 64 such that the lead screw member and the primary dose member are rotationally locked and slidable in relation to each other, FIGS. 2 and 3.

The device further comprises: —a locking member 96 fixedly connected to the housing and releasably connected to the lead screw member by co-acting locking means; —a first spring force means 48 arranged between the first inner wall 30 of the housing and the nut, wherein the first spring force means is in a pre-tensioned state when said locking means are engaged and the device is in the non-activated state; and —a secondary dose member 90 rotatably connected to said primary dose member 66 via a pinion gear 94, FIG. 3.

The device also comprises dose setting means connected to the primary dose member by co-acting fourth slidably-and-rotatably-locked means, such that when the device is to be set from the non-activated state to the activated state, the dose setting means are manually manipulated in a pre-determined direction, whereby the locking means are released and the lead screw member is distally moved a pre-determined distance by the first spring force means independent of the size of a dose to be set.

Figure 4:
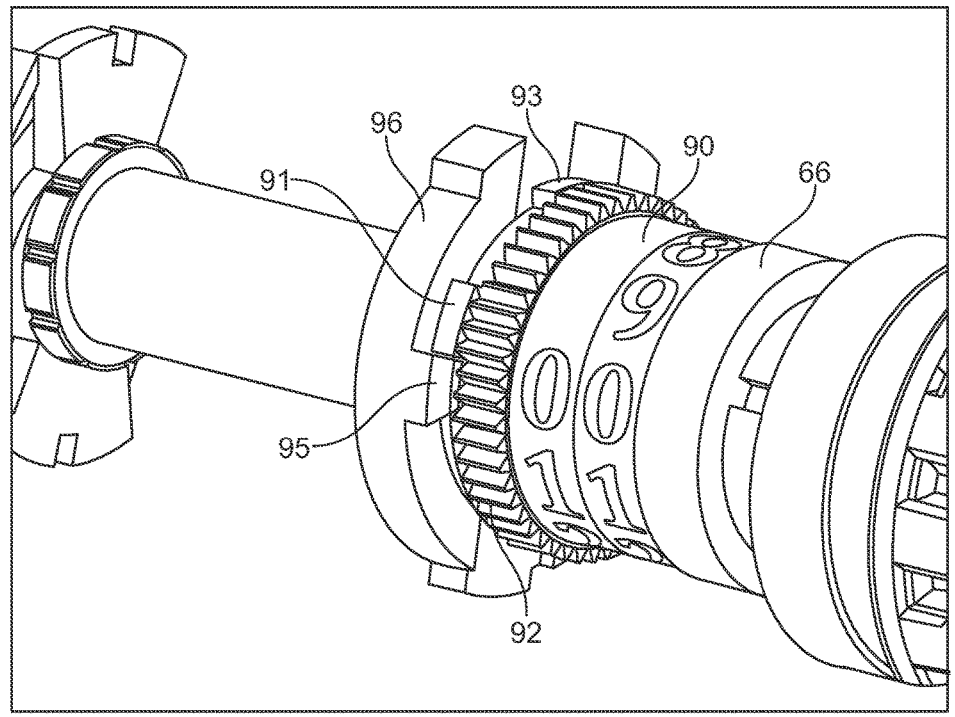
FIG. 4 is a further detailed view of the dose-setting mechanism comprised in the present invention.

The dose setting means comprises a clutch plate 74 provided with a first annular ratchet 76, a dose setting knob 84 provided with a second annular ratchet 82, and a second spring force means 78 arranged between a second annular inner wall 80 of the housing and a proximal surface of the clutch plate, such that clutch plate is distally urged and the first and the second ratchet are abutting each other, and which dose setting knob protrudes through the distal end of the housing, FIGS. 1a and 4. The fourth slidably-and-rotatably-locked means comprises longitudinally extending grooves 70 on the outer circumferential surface of the primary dose member 66, and radial inwardly directed protrusions 72 on the inner surface of the clutch plate 74, wherein the longitudinally extending grooves 70 cooperate with radial inwardly directed protrusions 72 such that the primary dose member and the clutch plate are rotationally locked and slidable in relation to each other, FIGS. 2 and 3. The distal end of the lead screw member 58 protrudes through the dose setting knob 84, and is at its distal end arranged with a dose injection button 86, FIGS. 2 and 7b. Outside the dose injection button 86 a spin ring 88 is rotatably arranged, FIG. 2.

The locking means comprises: —a proximally pointing and radial flexible lever 102 arranged on the locking member, —an annular ledge 62 on the circumferential surface of the lead crew member, and —the circumferential inner surface of the secondary dose member, FIG. 2. The secondary dose member 90 is also arranged with teeth 92 arranged around its circumference, which teeth cooperate with teeth on the pinion gear 94, which is journalled in the housing as well as the locking member 96 via a locking lever bracket, FIG. 3. Further the primary dose member 66 is arranged with a gear segment 98, which also cooperate with the pinion gear 94, FIG. 3. A certain part of the lead screw member 58 is arranged with the splines 60 on its outer circumferential surface, FIG. 2; which splines have a lesser diameter than the proximal part of the lead screw member, thereby creating the annular ledge 62, FIG. 2. The locking member 96 also comprises on its distal circumferential surface a distally pointing stop member 95, and the secondary dose member 90 comprises on its proximal circumferential surface a first 91 and a second 93 proximally pointing stop member arranged to interact with the stop member of the locking member, FIG. 4.

The proximal part of the primary dose member 66 and the secondary dose member 90 are arranged with a circumferential band containing numbers or indicia 68 which are used to indicate dose size through a dose window on the housing, as will be explained below, FIG. 3.

The device is intended to function as follows. When delivered to the user, the device is in the non-activated state wherein a medicament container 20 has been inserted in the medicament container holder 18 in the proximal end of the device, FIG. 1, the first spring force means is in a pre-tensioned state and said locking means are engaged, wherein the circumferential inner surface of the secondary dose member 90 forces the flexible lever 102 radial inwardly in contact with the ledge 62.

When the device is to be used the protective cap 26 is removed and the dose setting means are manually manipulated for setting the device from the non-activated state to the activated state by rotating the dose setting knob 84 counter clockwise until activating indicia as e.g. two zeros are visible through the window of the housing. The rotation of the dose setting knob 84 causes the clutch plate 74 and thereby the primary dose member 66 to rotate due to the engagement between the co-acting fourth slidably-and-rotatably-locked means, and due to the connection between the first 76 and the second 82 ratchets. However, the lead screw member is not rotated since the third slidably-and-rotatably-locked means 60, 64 are not in engagement, i.e. the splines 60 on the outer circumferential surface of the lead screw member and the corresponding splines 64 arranged on the inner circumferential surface of the primary dose member 66 are not in engagement. The secondary dose member 90 also rotates due to the connection between the gear segment 98 of the primary dose member 66 and the teeth 92 of the secondary dose member 90 through the pinion gear 94. The rotation of the secondary dose member 90 is stopped when its second proximally pointing stop member 93 abuts the distally pointing stop member 95. This causes a longitudinal groove on the inner circumferential surface (not shown) of the secondary stop member to be aligned with the flexible lever 102 whereby the flexible lever is radial outwardly flexed into the groove and thereby moved out of contact with the ledge 62 of the lead screw member 58. This causes the lead screw member 58 to move a pre-determined distance in the distal direction due to the force of the spring 48 acting on the nut 44, which in turn is attached to the lead screw member 58. The splines 60 on the outer circumferential surface of the lead screw member and the corresponding splines 64 arranged on the inner circumferential surface of the primary dose member are then engaged to each other. Because of the movement of the nut 44, the plunger rod 36 is also moved. The distal end of the lead screw member 58 and its dose injection button 86 now protrude distally out of the housing said predetermined distance and independent of the size of the dose to be set.

The device is now in the activated state and ready for setting a required dose of medicament, FIGS. 7a and 7b.

When setting a dose, the plunger rod is arranged to be proximally moved a distance corresponding to a set dose to be delivered by manually manipulating the dose setting knob. The dose setting knob 84 is rotated in the clockwise direction which also rotates the primary dose member 66 clockwise indicating the dose that is being dialled. At the same time the primary dose member 66 rotates the lead screw member 58 clockwise due to the engagement between the co-acting third slidably-and-rotatably-locked means 60, 64; and the lead screw rotates the plunger rod due to the engagement between the co-acting first slidably-and-rotatably-locked means, driving the plunger rod 36 through the nut 44 because of the threaded engagement between them, thereby moving the plunger rod 36 proximally. The secondary dose member 90 also rotates due to the connection between the gear segment 98 of the primary dose member 66 and the teeth 92 of the secondary dose member 90 through the pinion gear 94. The rotation of the secondary dose member 90 is stopped when its first proximally pointing stop member 91 abuts the distally pointing stop member 95, which indicates the maximum dose the device can deliver e.g. two indicia as e.g. a seven and a zero are visible through the dose window. In any case, the set dose is visible through the dose window of the housing. At this point the device is ready for an injection.

Moreover, if the user attempts to dial past the maximum dose the device can deliver or if the user attempts to dial pass the activating indicia, the connection between the first annular ratchet 76 and the second annular ratchet will function as a clutch.

Figure 8A:
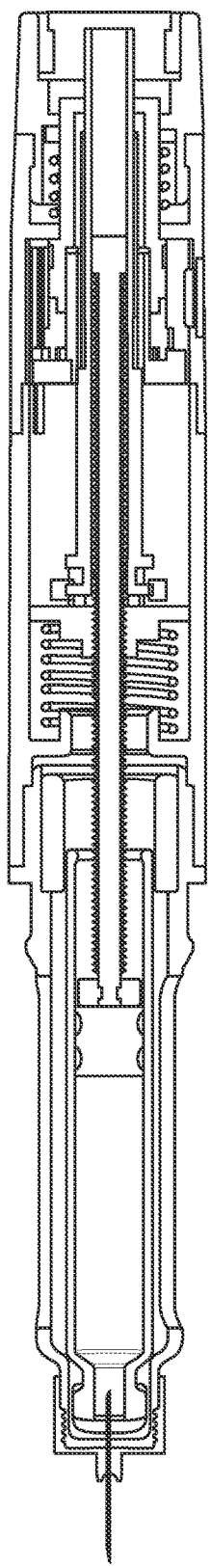
Figure 8B:
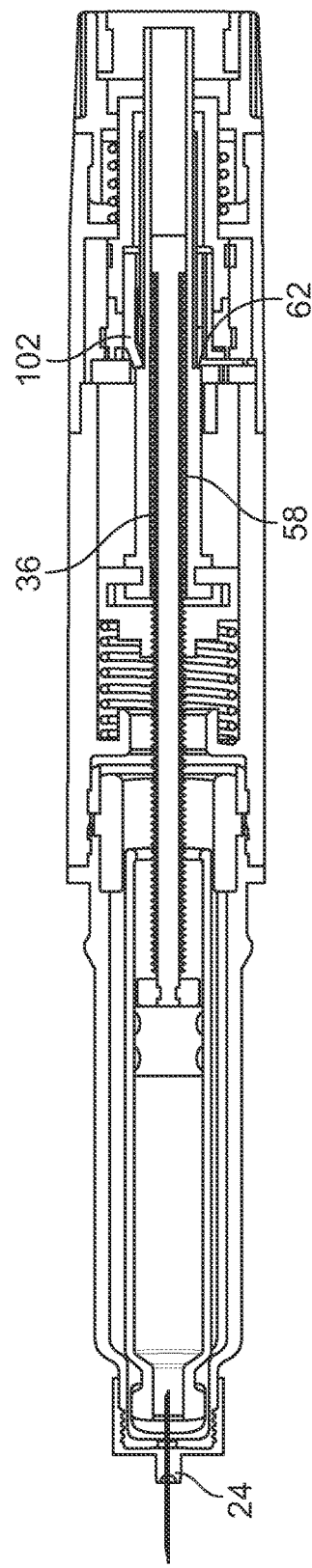
Figure 9:
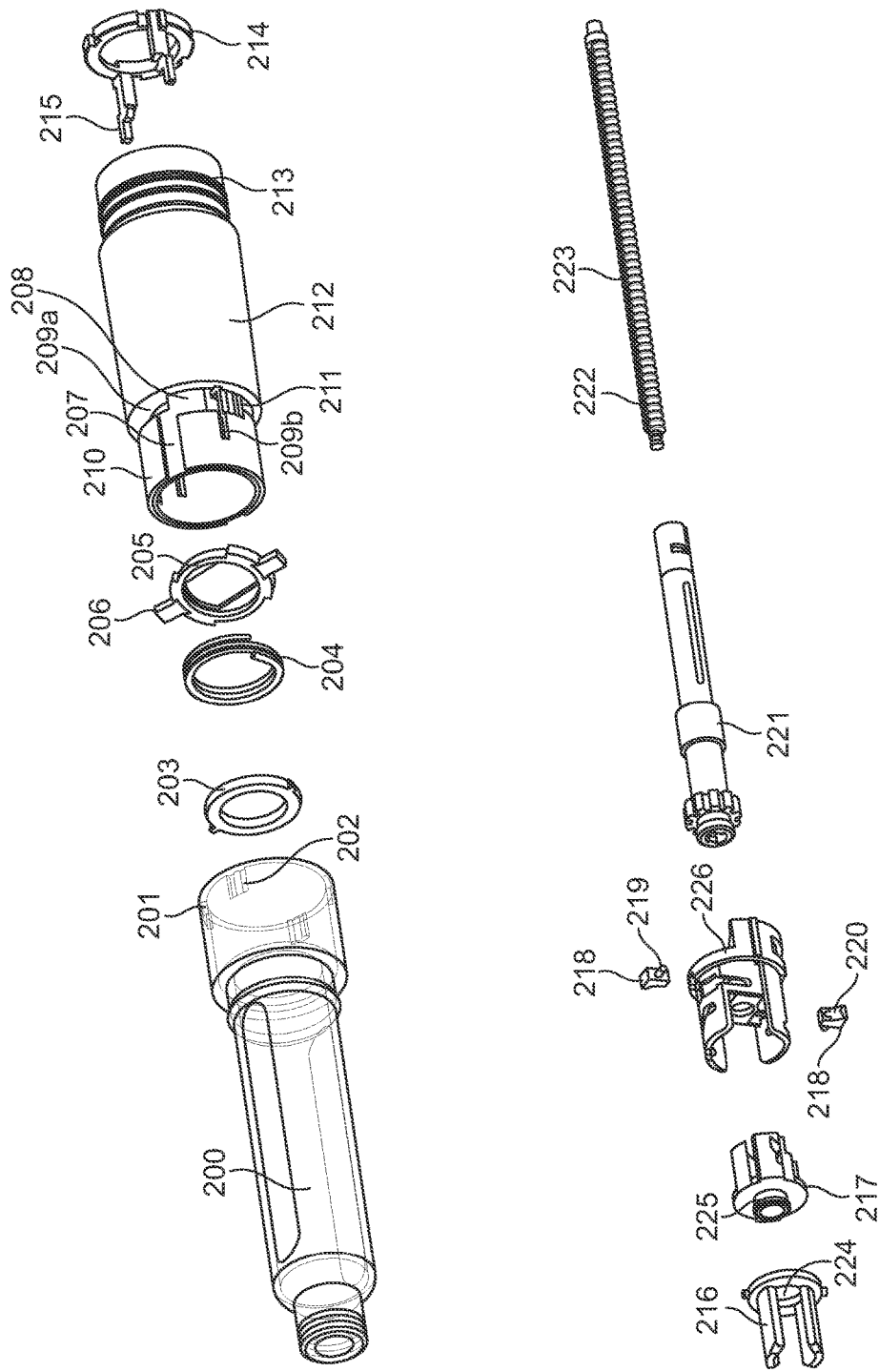
FIG. 9 is an exploded perspective view of one possible embodiment of the resetting mechanism that can be connected to the dose-setting mechanism illustrated in FIGS. 1-8.
Figure 10A:
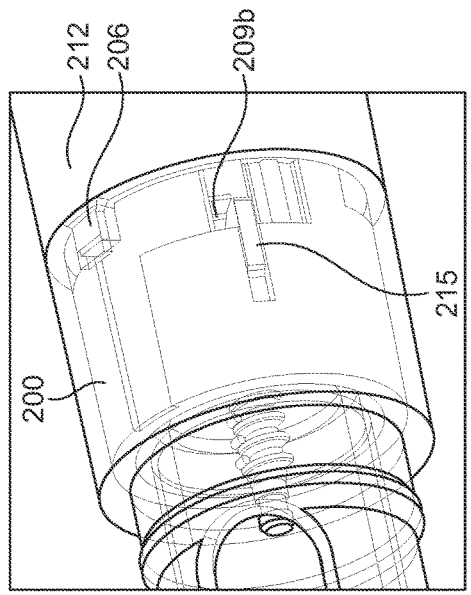
FIGS. 10a and 10b are perspective view of the distal end of the cartridge holder that can be attached to the resetting mechanisms of this disclosure.
Figure 10B:
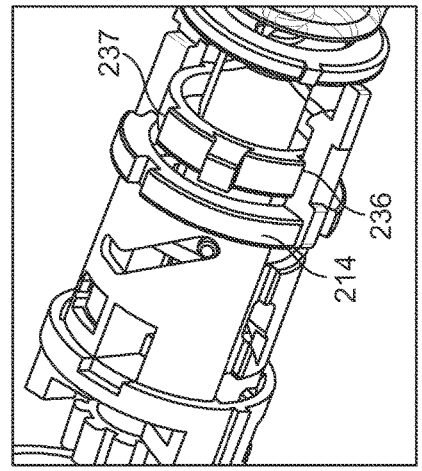
Figure 10A:
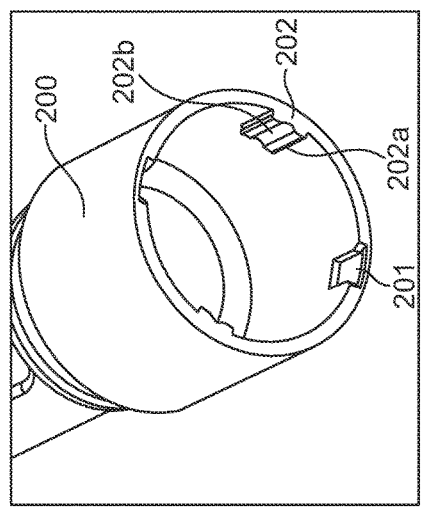
Figure 11:
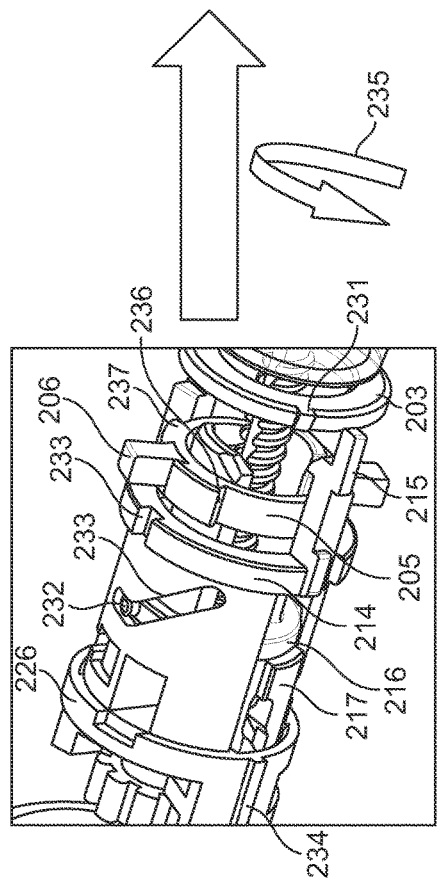
FIG. 11 shows a perspective view of the components of the resetting mechanism of FIG. 9 transitioning from a locked to an unlocked state.

When the dose is set, a medicament delivery member 24 is attached to the proximal end of the device, such as e.g. an injection needle. It is however to be understood that other types of medicament delivery members may be used in order to deliver a dose of medicament. The medicament delivery member is then placed at the delivery site and the user presses the dose injection button 86 in the proximal direction the predetermined distance that the distal end of the lead screw member 58 and its dose injection button 86 protrudes distally out of the housing and which said predetermined distance is independent of the size of the dose to be delivered. This causes the lead screw member 58 to move in the proximal direction as well as the nut 44 and the plunger rod 36. This proximal movement of the plunger rod 36 causes it to act on the stopper 38 of the medicament container 20 whereby a dose of medicament is expelled through the medicament delivery member 24. When the lead screw member 58 has reached a certain distance inside the housing, the flexible lever 102 of the locking member is again moved in contact with the ledge 62 of the lead screw member 58, FIG. 8. The medicament delivery member may now be removed and discarded.

When a subsequent dose is to be performed, the above described procedure is performed and can be repeated until the medicament container or cartridge is emptied. When the cartridge is empty it is preferable that the delivery device have the capability to allow the empty cartridge to be replaced with a new full cartridge. Thus, it is desirable for the delivery device to have a resetting mechanism whereby the proximally extended threaded plunger rod can be pushed distally to reset the dose setting mechanism and to make room for a new cartridge where the cartridge bung or piston is at the distal end of the cartridge.

One possible embodiment of a plunger rod resetting mechanism for a drug delivery device includes that illustrated in FIGS. 9-13. FIG. 1 illustrates an exploded view of the plunger rod resetting mechanism where a front housing 212 has an outer surface 210 on a proximal end configured to allow removable attachment of a cartridge holder 200 through engagement of a snap fit connector 211 on the outer surface. The connector 211 engages a cooperating connector 202 on the distal end of holder 200. FIG. 10a shows the connector 202 on the inside portion of the holder 200 interior portion, where the connector 202 has a radial stop 202a and a rib 202b configured to engage a corresponding detent on connector 211. The inside portion of holder 200 also has one or more slots 201 configured to engage radial protruding pins 206 on locking shell 205. Locking shell 205 is located inside housing 212 such that the pins 206 project through slots 209a in the outer surface 210.

The cartridge holder 200 is attached to front housing 212 by aligning connector 202 with longitudinal slot 207 in the outer surface 210 and pushing the holder 200 axially in the distal direction until the connector 202 reaches the end of slot 207. This aligns slots 201 with protruding pins 206 on locking shell 205. (see FIG. 10b). Holder 200 is then rotated within transverse slot 208 to engage connectors 211 and 202. At the same time the rotation of the cartridge holder 200 causes rotation of locking shell 205 because slots 201 and pins 206 rotate together. As locking shell 205 rotates so does transfer ring 216 because the internal portion of locking shell 205 is configured to be rotationally fixed to the transfer ring but at the same time allowing the transfer ring to move axially relative to the locking shell. Because the pins 206 project through the house outer surface 210, the locking shell is axially fixed to the housing 212. Housing 212 also has a connector 213 at the distal end for connection and cooperation with a dose setting mechanism as described above.

A lock pin 214 is located inside housing 212 and is rotationally fixed to the housing through engagement of slot 230 with a radially projecting rib inside of housing 212. Lock pin 214 has one or more axially movable stops 215 that project through opening 209a in the outer surface 210. The moving stop 215 moves from a proximal position to a distal position as the dose setting mechanism changes from a non-activated state to an activated state. When the dose setting mechanism is in the non-activated state the dose button is in its most proximal position (i.e., it is pushed in). When the dose setting mechanism is in the activated state the dose button is in its most distal position (i.e., it is popped out of distal end of the device housing) as illustrated in FIGS. 7a & 7b. When the dose button is in the most distal position the lock pin is biased and moved distally by biasing member 204, shown as a compression spring, but could be a spring washer or other structural component capable of exerting a biasing force. As the lock pin is moved distally so are the stops 215 projecting through opening 209b. This distal movement of the stops 215 causes the stops to about radial stop 202a. This abutment of stops 202a and 215 prevents cartridge holder 200 from being rotated and removed from front housing 212.

The biasing member 204 also exerts a biasing force in the proximal direction against the distal side of push plate 203 that is rotationally fixed to the inside of housing 212 through engagement of radially extending pins 231 with cooperating slots inside of the housing. The proximal biasing force on push plate 203 is transferred directly to the distal end of a cartridge loaded into cartridge holder 200 causing the cartridge to be pushed against the proximal end of the cartridge holder 200. This ensures that the cartridge is properly seated within the holder and prevents any rattling or other unwanted movement of the cartridge within the holder.

The transfer ring 216 is connected to push pin 217 through cooperating connectors 224 and 225. Connectors 224 and 225 are configured to axially fix the transfer ring and push pin so that when the transfer ring moves axially the push pin moves with it. Although connectors 224 and 225 axially fix the transfer ring and push pin to each other, connectors 224, 225 also are configured to allow the transfer ring to rotate relative to the push pin as the transfer ring moves axially in the proximal direction. Push pin 217 is rotationally fixed relative to housing 212.

A cam nut 226 is engaged with the transfer ring 216 through a camming connection 232, 233 (see FIG. 11) that allows the transfer ring to rotate and move axially relative to the cam nut 226, which is axially fixed to the housing 212 through engagement of spline 234 with a corresponding or cooperative spline or groove on the inside of housing 212. Transfer ring 216 is rotated in the direction of arrow 235 when pins 206 are rotated in the same direction as the cartridge holder 200 is rotated to remove it from the housing 212. As locking shell 205 is rotated, the rotational stop 237 is moved out of engagement with lock pin 214 until a second rotational stop 236 moves into engagement with lock pin 214. Because the locking shell is rotationally fixed to the transfer ring, rotation of the locking shell causes rotation of the transfer ring 216. The camming connection 232, 233 between the transfer ring and the rotationally fixed cam nut 226 causes the transfer ring 216 to translate in the proximally direction 246 (see FIG. 12) as it is being rotated by the locking shell 205.

Figure 12:
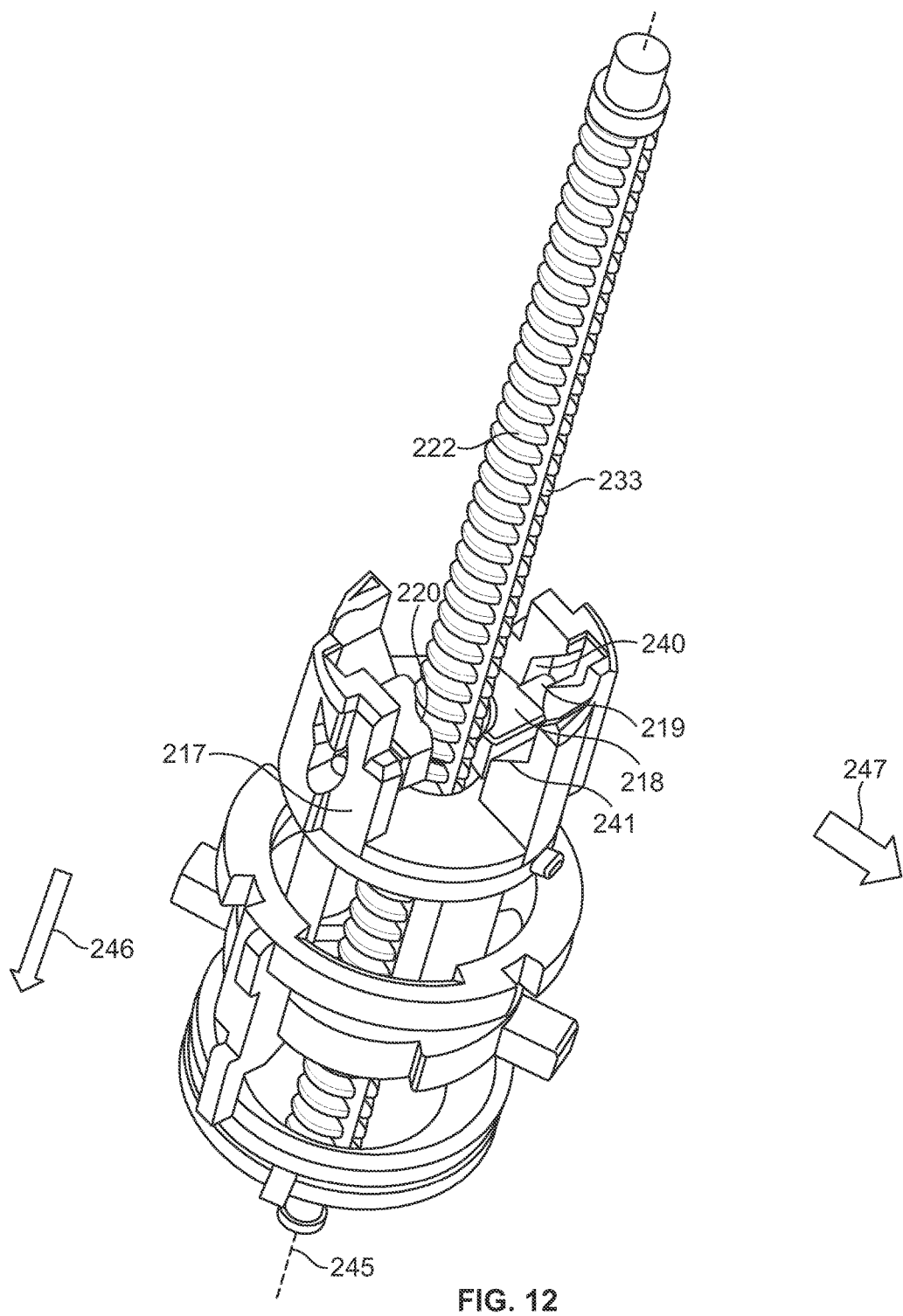
FIG. 12 is a partial perspective view of the resetting mechanism shown in FIG. 9 illustrating the nut segments in a locked position.
Figure 13:
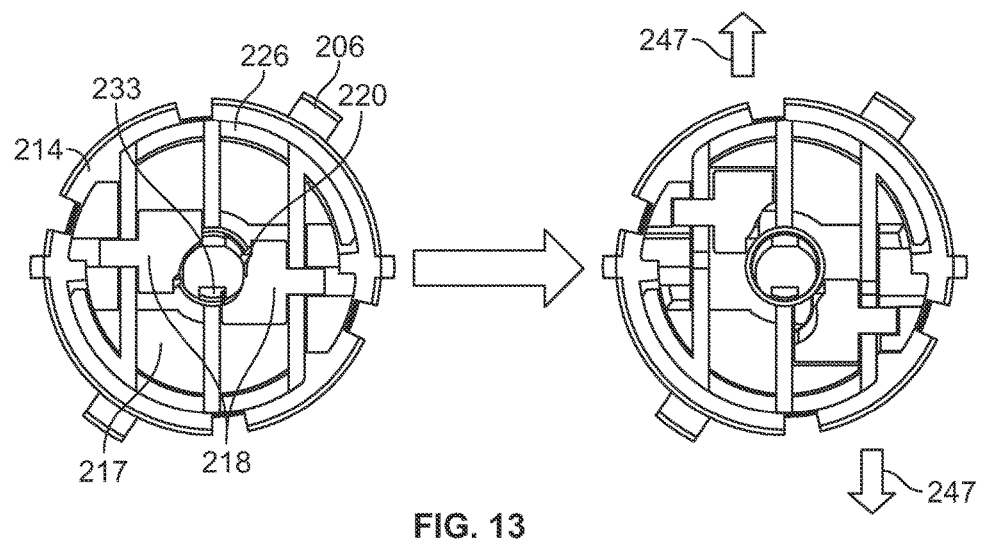
FIG. 13 is a cross-sectional view of the resetting mechanism of FIG. 9 showing the transition from a locked to an unlocked state.

The axial translation of the transfer ring 216 pulls push pin 217 axially in the same direction because they are axially fixed to each other. As the push pin 217 is pulled proximally a camming engagement 219, 240 between nut segments 218 and push pin 217 cause the nut segments move transversely relative to the longitudinal axis 245 of plunger rod 233 (see FIG. 12). The axial movement of the push pin in the proximal direction 246 causes the nut segments 218 to ride up ramp 241 and move transversely in direction 247. This transverse movement 247 disengages the threaded engagement 220 between the nut segments 218 and the threaded outer surface 222 of plunger rod 233. It is noted that the nut segments do not move axially and do not move radially relative to the longitudinal axis 245, but only transversely in direction 247. The nut segment 218, preferably two nuts segment arranged diametrically opposite to each other relative to axis 245 and plunger rod 233. As illustrated in FIG. 12, the nut segments are in locked position where they are in a threaded engagement with threads 222 on the outer surface of plunger rod 233. As the camming connection 219, 240 causes the nut segments to move transversely the threaded connection is disengaged and the nut segments move to an unlocked position. The locked and unlocked positions are shown in the cross-sectional view of the resetting mechanism illustrated in FIG. 13.

Figure 14:
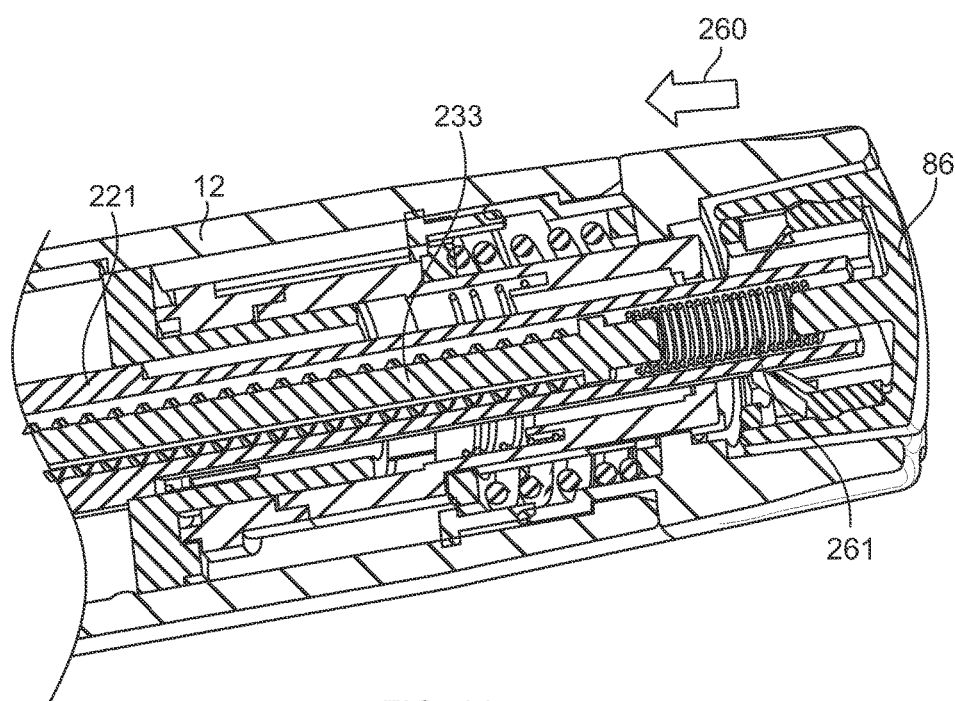
FIG. 14 is a partial cross-sectional perspective view of the distal end of the drug delivery device.

When the nut segments 218 are moved to the unlocked position the cartridge holder 200 can be removed from the resetting mechanism and the user can manually push the plunger rod 233 back into the dose setting mechanism in a distal direction. As illustrated in FIG. 14, the plunger rod is positioned inside of lead screw 221 and is engaged with a proximal end of a biasing member, shown for example, as spring 261. Biasing member 261 exerts a biasing force in the distal direction represented by directional arrow 260. This biasing force ensures that the proximal end of the plunger rod 233 remains in contact or abutment with the distal end of the slidable stopper 38 inside the medicament container/cartridge 20. Once the plunger rod has been retracted into the dose setting mechanism, then a new cartridge of medicament with an internal piston or bung at distal end thereof can be inserted into the cartridge holder and the cartridge holder reconnected to the resetting mechanism. Reattaching the cartridge holder reverses the above-described movement of the components of the resetting mechanism such that the nut segments 218 move transversely in opposite direction from direction 247 to go from the unlock position to the locked position where the nut segments again become threadedly engaged with the plunger rod.

The foregoing description of the specific embodiments will reveal the general nature of the disclosure so others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

The invention claimed is:

1. A plunger rod resetting mechanism for a drug delivery device comprising,
   a) a housing having an outer surface on a proximal end configured to allow removable attachment of a cartridge holder through engagement of a snap fit connector on the outer surface;
   b) a locking shell positioned inside the housing and having a radial projecting pin protruding through the outer surface of the housing, where the locking shell is rotatable relative to the housing and configured to engage the cartridge holder during attachment to the housing;
   c) a lock pin rotationally fixed to the housing and having a stop projecting through the outer surface of the housing and slidable in the distal direction from an unlocked to a locked position where the stop prevents removal of the cartridge holder from the housing;
   d) a biasing member that exerts a distal force on the lock pin to move the stop from the unlocked to the locked position;
   e) a transfer ring rotationally fixed to and axially slidable to the locking shell;
   f) a cam nut engaged with the transfer ring through a cam that allows the transfer ring to rotate and move axially relative to the cam nut;
   g) a push pin axially fixed to the transfer ring; and
   h) a nut segment slidably connected to the push pin through a cam, where the nut segment is configured to move from a locked position to an unlocked position.

2. The resetting mechanism of claim 1 further comprising a push plate to transfer a proximal biasing force to a cartridge contained in a cartridge holder.

3. The resetting mechanism of claim 2 where the biasing member is a compression spring located between the push plate and the lock pin.

4. The resetting mechanism of claim 1 where resetting mechanism comprises two nut segments that are threadedly engaged with an outer surface of a plunger rod having a longitudinal axis when in the locked position and are disengaged from the plunger rod when the nut segments are in the unlocked position.

5. The resetting mechanism of claim 4 where the nut segments are engaged with the push pin such that nut segments simultaneously move transversely relative to the longitudinal axis of the plunger rod when the push pin moves axially causing the nut segments to move from the locked to the unlocked position.

6. The resetting mechanism of claim 1 further characterized in that the lock pin is rotationally fixed to the housing.

7. An assembly of a dose setting mechanism and a resetting mechanism for a medicament delivery device comprising, a) a dose setting mechanism comprising,
   a rear housing having a longitudinal axis;
   a locking member fixedly connected to the rear housing and configured to be in a locked position when the dose setting mechanism is in a non-activated state and in an unlocked position when the dose setting mechanism is in an activated state; and
   a pinion connected to the locking member and having an axis of rotation offset and parallel to the longitudinal axis; and
b) a resetting mechanism comprising,
   a front housing having an outer surface on a proximal end configured to allow removable attachment of a cartridge holder through engagement of a snap fit connector on the outer surface;
   a locking shell positioned inside the front housing and having a radial projecting pin protruding through the outer surface of the housing, where the locking shell is rotatable relative to the front housing and configured to engage the cartridge holder during attachment to the front housing;
   a transfer ring rotationally fixed to and axially slidable to the locking shell;
   a cam nut engaged with the transfer ring through a cam that allows the transfer ring to rotate and move axially relative to the cam nut;
   a push pin axially fixed to the transfer ring; and
   a nut segment slidably connected to the push pin through a cam, where the nut segment is configured to move from a locked position to an unlocked position.

8. The assembly of claim 7 where the resetting mechanism further comprises a lock pin rotationally fixed to the front housing and having a stop projecting through the outer surface of the front housing and slidable in the distal direction from an unlocked to a locked position where the stop prevents removal of the cartridge holder from the front housing.

9. The assembly of claim 8 where the resetting mechanism further comprises a biasing member that exerts a distal force on the lock pin to move the stop from the unlocked to the locked position.

10. The assembly of claim 8 where the dose setting mechanism further comprising a dose knob that protrudes through a distal end of the housing when in a first axial position when the dose setting mechanism is in the non-activated state and in a second axial position when the dose setting mechanism is in the activated state.

11. The assembly of claim 10 further characterized in that the lock pin is in the locked position when the dose knob is in the second axial position, where the first axial position is less than the second axial position measured relative to the distal end of the housing.

12. The dose setting mechanism of claim 7 further comprising a primary dose member and a secondary dose member, each having numbers visible on an outside surface.

13. The dose setting mechanism of claim 12 further characterized in that the dose setting mechanism changes from the non-activated state to the activated state when a number zero on the primary dose member aligns with a number zero on the secondary dose member and the aligned zeros are visible through a window in the housing.

14. A method of resetting a drug delivery device comprising,
   a) placing a dose setting mechanism in a non-activated state;
   b) rotating a cartridge holder relative to a front housing of a resetting mechanism causing rotation of a locking shell within the front housing;
   c) rotating a transfer ring simultaneously with the rotation of the locking shell to cause the transfer ring to move axially in the proximal direction relative to the locking shell following a cam track connecting the transfer ring to a cam nut that is rotationally fixed to the front housing;
   d) moving a push pin axially in the proximal direction as a result of the axially fixed connection to the transfer ring;
   e) moving nut segments from a locked position to an unlocked position as a result of a cammed engagement with the push pin;
   c) pulling the cartridge holder axially in the proximal direction to remove it from the front housing;
   d) pushing a plunger rod having a longitudinal axis axially in a distal direction to reset the drug delivery device such that a new cartridge of medicament can be loaded into the cartridge holder and the cartridge holder reattached to the front housing.

15. The method of claim 14 where the nut segments are threadedly engaged with an outer surface of the plunger rod when in the locked position and are disengaged from the plunger rod when the nut segments are in the unlocked position.

16. The method of claim 15 the nut segments are engaged with the push pin such that nut segments simultaneously move transversely relative to the longitudinal axis of the plunger rod when the push pin moves axially causing the nut segments to move from the locked to the unlocked position.

* * * * *